United States Patent [19]
Birnbaum

[11] Patent Number: 5,464,021
[45] Date of Patent: Nov. 7, 1995

[54] TELEMETRIC TRANSMITTER UNIT

[75] Inventor: Burton H. Birnbaum, Woodmere, N.Y.

[73] Assignee: Polar Electro Oy, Kempele, Finland

[21] Appl. No.: 323,224

[22] Filed: Oct. 14, 1994

[51] Int. Cl.[6] ........................................ A61B 5/04
[52] U.S. Cl. .................. 128/696; 128/644; 128/690; 128/903
[58] Field of Search .................... 128/639, 644, 128/690, 696, 903

[56] References Cited

U.S. PATENT DOCUMENTS

| | | | |
|---|---|---|---|
| 3,420,223 | 1/1969 | Day et al. | 128/639 |
| 3,572,316 | 3/1971 | Vogelman et al. | 128/903 |
| 3,972,320 | 8/1976 | Kalman | 128/690 |
| 4,121,573 | 10/1978 | Crovella et al. | 128/903 |
| 4,516,581 | 5/1985 | Sessions | 128/639 |

FOREIGN PATENT DOCUMENTS 9316636  9/1993  WIPO ........................ 128/692

*Primary Examiner*—William E. Kamm
*Attorney, Agent, or Firm*—Burns, Doane, Swecker & Mathis

[57] ABSTRACT

The invention relates to a telemetric transmitter unit comprising electrodes for placement against the body of a person wearing the telemetric transmitter unit for detecting heartbeat signals of said person. The plastic members joining the transmitter and electrodes together so as to form an integrated casing for the transmitter unit has a bottom side exposing the surface of the electrodes, whereby the electrodes are provided with holes, each hole being associated to a fluid channel leading to an opening in the casing. A fluid applied to an opening in the casing flows through the hole in the electrode, thus wetting, at least in the part of the body lying underneath the electrode, any cloth or garment on the wearer as well as the skin, in order to provide a conductive path for the heart beat signals between the skin of the wearer and the electrode through said cloth or garment.

4 Claims, 1 Drawing Sheet

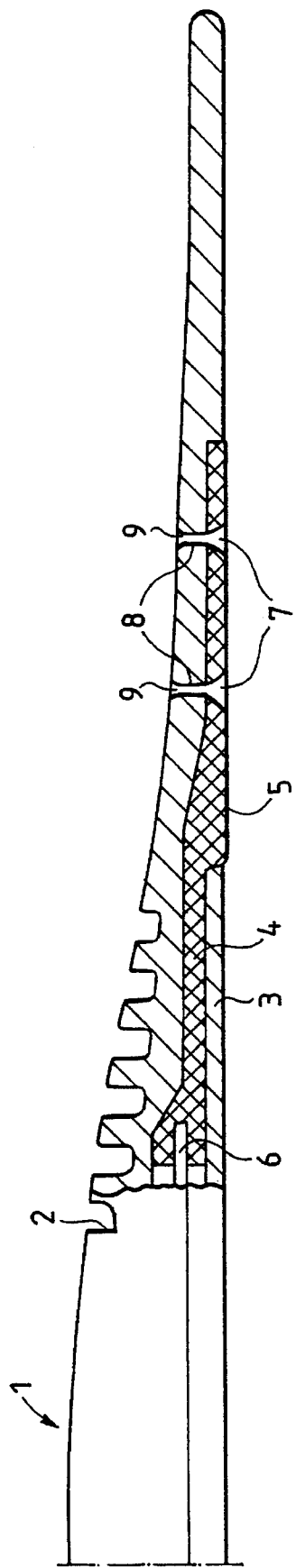
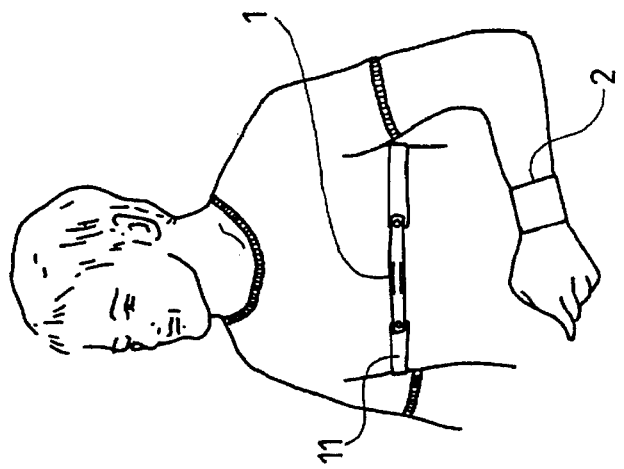
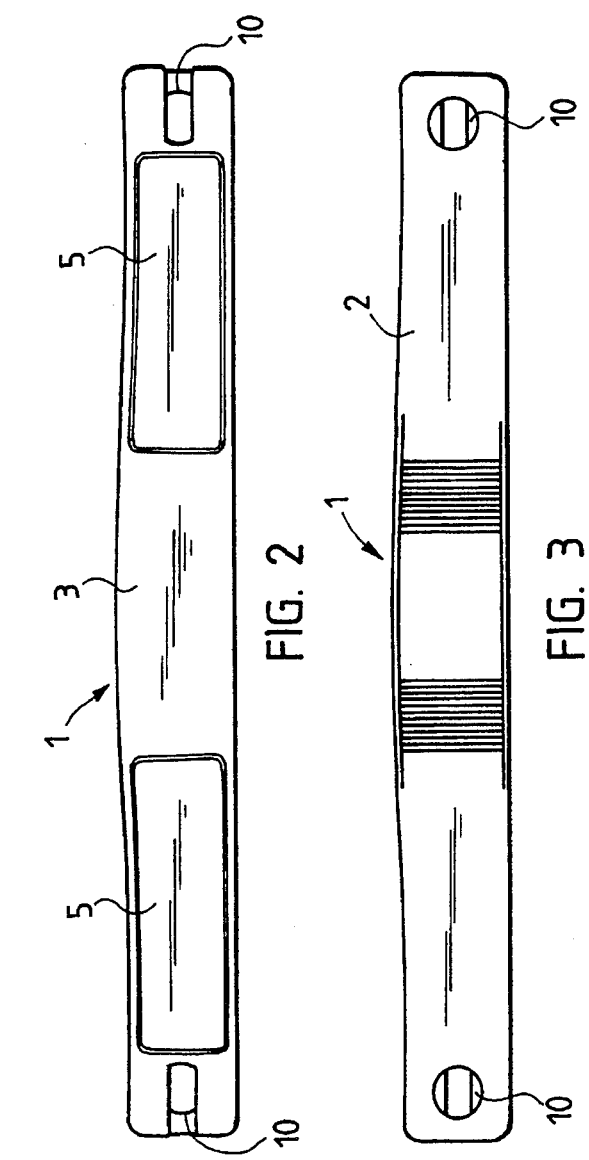

TELEMETRIC TRANSMITTER UNIT

FIELD OF THE INVENTION

The present invention relates to a telemetric transmitter unit for transmitting heartbeat signals. Such transmitters receive and process signals detected by one or several electrodes, and transmits the heartbeat data further to a separate receiver by using a magnetic proximity field.

BACKGROUND OF THE INVENTION

Telemetric data transmission techniques are known from the telemetric measuring device described in the U.S. Pat. No. 4,625,733 to Säynäjäkangas, the subject matter of which is incorporated herein by reference. Such equipment is used for detecting and telemetric transmission of heartbeat and EKG signals to a separate wrist-worn receiver, measurement and display device, to be used for personal heartbeat rate monitoring during exercise and sports activities. The telemetric transmitter mainly consists of transmitter electronics encapsuled in a casing and fastened to a belt holding the transmitter in place and of electrodes electrically connected to the transmitter electronics and located on the surface of the belt towards the user's skin on both sides of the transmitter electronics.

In the copending U.S. patent application Ser. No. 07/885,607, belonging to the assignee of the present application, is shown an improved telemetric transmitter unit, where the telemetric transmitter unit is coupled to the electrodes by means of a conductive plastic layer. In fact, the electrodes themselves may be formed as a part of the conductive plastic layer. The transmitter electronics and the conductive plastic layers are molded or jointed together with plastic material to form an integrated, waterproof transmitter unit.

The prior art telemetric transmitter units, which are used for heartbeat rate monitoring during exercise and sport performance, are more or less invariably attached to the chest of the user by means of elastic straps connected to the transmitter unit and tied more or less tightly around the upper body of the user. The electrodes and thus the whole assembly of the transmitter unit and the straps are attached in direct contact with the skin of the user, in order to ensure proper contact of the electrodes with the skin of the user and thus proper operation and measuring from the beginning of the performance or measuring cycle.

This direct contact of the electrodes with the user's skin is not desirable. The material of the electrodes must be subject of careful design considerations in order to avoid any allergic reactions to the electrode material. Skin chafing due to the sliding of the electrode belt and the electrodes on the body during extensive motion over long periods is another problem. In sports clubs and events, where many individuals may be tested using the same equipment, dermatological disease transfer may occur from one user to another. A very frequent washing of the electrode belts, on the other hand, reduces the life of the elastic straps of the electrode belt.

OBJECT OF THE INVENTION

It is an object of the present invention to provide an improved telemetric transmitter unit, which may be worn over a shirt or any suitable garment protecting the user's skin from having direct contact with the transmitter unit and the electrode belt. It is a further object of the invention to provide a telemetric transmitter unit with means to at least substantially compensate for the reduction of the sensitivity of the electrode when separating their surface from the skin of the user by a shirt or the like.

SUMMARY OF THE INVENTION

The telemetric transmitter unit according to the present invention mainly comprises a couple of electrodes which are placed against the chest of a person wearing the telemetric transmitter. The telemetric transmitter is electrically connected to the electrodes to receive signals from them and for processing the signals electronically, in order to generate a variable magnetic proximity field to telemetrically transmit heartbeat rate data to a separate receiver. The telemetric transmitter unit has an integrated casing with a bottom side exposing the surface of the electrodes. At least one of the electrodes is provided with at least one hole, each hole being associated to at least one fluid channel leading to at least one opening in the casing, whereby fluid applied to said opening in the casing is allowed to flow through said hole in the electrode, thus wetting the shirt of the wearer as well as the skin, in order to provide a conductive path for the heart beat signals between the skin of the wearer and the electrode through the shirt.

The advantages of the telemetric transmitter unit according to the present invention are numerous:

being able to wear the unit over the shirt and not directly against the skin prevents allergic reactions against the electrode material and irritation of the skin during long-term use. Dermatological disease transfer is minimized where belts are shared among many individuals, such as in health clubs or in schools, since the electrodes never touch the skin. The transfer of perspiration to the elastic straps used to keep the electrodes in place while exercising is greatly reduced, which eliminates washing cycles and increases the life of the elastic strap.

Discomfort of wearing a wetted garment or shirt is minimized, because the squirted fluids only wet the area under the electrodes. Those areas normally are wetted by perspiration anyway. Correct operation of the telemetric transmitter unit through a shirt due to perspiration is possible, but cannot be guaranteed, and will in any case not occur until some half an hour after starting an exercise.

BRIEF DESCRIPTIONS OF THE DRAWINGS

The preferred embodiments of the invention will be described below with reference to the attached drawings, in which FIG. 1 is a partial cross-section of a part of a telemetric transmitter according to the invention from the side, FIG. 2 shows the telemetric transmitter of the invention from below, FIG. 3 shows the telemetric transmitter of the invention from above, FIG. 4 is a cross-section of the telemetric transmitter of the invention,

DETAILED DESCRIPTION OF PREFERRED EMBODIMENTS

A telemetric transmitter unit according to the present invention, constructed according to the enlarged view of half of the transmitter unit of FIG. 1 (the other half being symmetrical), comprises a casing of plastic parts 2 and 3 encapsulating a printed circuit board 6, which carries the electronic circuits of the telemetric transmitter unit, a conductive plastic material 4, which interconnects the downward faced surfaces 5 of said conductive plastic material to the circuit board 6 of the transmitter electronics. The surfaces 5 actually forms the electrodes. The plastic parts or layers 2 and 3, the conductive plastic material 4 and the transmitter electronics are molded or jointed together in order to form an integrated, and preferably waterproof telemetric transmitter unit 1.

The signals detected by the electrodes 5 are transmitted telemetrically, i.e. wirelessly to a separate receiver by means of a transmitter coil by using a variable magnetic proximity field, as disclosed in the aforementioned U.S. Pat. No. 4,625,773, which relates to the detection of EKG and heartbeat signals e.g. from the chest of a sportsman. It also relates to the transmission of amplified signals to a wrist receiver, by means of which the sportsman can follow the development of the pulse. There can be also other signals to be transmitted, such as blood pressure information, and the transmitter can be positioned on any place on the skin of a person where detectors can detect the signals desired.

According to the invention, the electrode material 4 is provided with at least one hole 7, in FIG. 1 two such holes are shown. The holes are connected to fluid channels 8 leading to openings 9 on the upper side of the transmitter unit 1. Any suitable conductive fluid, such as a saline solution, which is applied to the opening 9 on the upper side of the transmitter unit, will thus flow through channel 8 and the hole 9 in the electrode material, and will eventually wet the the part of the user's skin and shirt which lies underneath the electrode 5. This will provide a conductive path for the heart beat signals between the skin of the wearer and the electrode through the shirt, and ensure immediate and correct operation of the pulse measuring device even if the user has strapped the unit over his or her shirt.

FIGS. 2 and 3 show the structure of the transmitter as a whole, FIG. 2 showing it from below and FIG. 3 from above. The transmitter has been formed to a band-like structure provided with means 10 at the ends thereof to be fastened to a carrying belt of the user. The plastic layers 2, 3 can be formed of a relatively soft polyurethane in order to provide elasticity. The two electrodes 5 are positioned symmetrically on both sides of the central part of the telemetric transmitter unit 1 in openings made in the lowermost plastic layer 3 of the transmitter unit, in order to come into contact with the user.

The conductive plastic layer connecting the transmitter electronics to the electrodes may be preferably formed of polyurethane, so that the plastic qualities to be joined together have a similar structure and thus form a structure as tight as possible. According to other embodiments of the invention, the conductive material 4 may be replaced by metallic electrodes or by a conductive elastomeric material. Furthermore, the plastic casing of the transmitter unit may as well be molded in a single piece of the same material. The essential feature of the transmitter unit is that it essentially consists of a top side, two side walls and a bottom side, which exposes the surfaces 5 of the electrodes against the user.

FIG. 4 shows the telemetric transmitter unit 1 of the invention when fastened to a carrying belt 11 and tightened around the chest of the user.

It is evident for one skilled in the art that the various embodiments of the invention are not restricted to the examples presented above, but that they can vary freely within the scope of the claims given below.

I claim:

1. A telemetric transmitter unit comprising:

at least one electrode for placement against a part of the body of a person wearing said telemetric transmitter unit for detecting heartbeat signals from said person;

an electronic circuit electrically connected to said at least one electrodes to receive signals from the electrodes, and for processing said received signals electronically in order to generate a variable magnetic proximity field for telemetric transmission of the detected heartbeat signals of said person to a separate receiver;

one or more plastic members joining the transmitter and electrodes together so as to form an integrated casing for the transmitter unit having a bottom side exposing the surface of the said at least one electrodes, wherein at least one of the electrodes is provided with at least one hole, each hole being associated to at least one fluid channel leading to at least one opening in said casing, whereby fluid applied to said at least one opening in the casing is allowed to flow through said hole in the electrode, thus wetting, at least in the part of the body lying underneath the electrode, any cloth or garment on the wearer as well as the skin, in order to provide a conductive path for the heart beat signals between the skin of the wearer and the electrode through said cloth or garment.

2. A telemetric transmitter unit according to claim 1, wherein said electrodes are made of an electrically conductive plastic material.

3. A telemetric transmitter unit according to claim 1, wherein said electrodes are made of an electrically conductive metal.

4. A telemetric transmitter unit according to claim 1, wherein said electrodes are made of an electrically conductive elastomeric material.

\* \* \* \* \*